US008903473B2

(12) United States Patent
Rogers et al.

(10) Patent No.: US 8,903,473 B2
(45) Date of Patent: Dec. 2, 2014

(54) RADIOPAQUE MARKERS FOR IMPLANTABLE MEDICAL DEVICES

(75) Inventors: Charles R. Rogers, Maple Grove, MN (US); David D. Differding, Edina, MN (US); John M. Gray, Brooklyn Park, MN (US); Michael J. Baade, Zimmerman, MN (US); Katherine J. Bach, Arden Hills, MN (US); Steven D. Byland, Coon Rapids, MN (US); Steven T. Deininger, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 226 days.

(21) Appl. No.: 13/282,301

(22) Filed: Oct. 26, 2011

(65) Prior Publication Data

US 2012/0065503 A1    Mar. 15, 2012

Related U.S. Application Data

(63) Continuation-in-part of application No. 12/882,786, filed on Sep. 15, 2010.

(51) Int. Cl.
*A61B 6/00* (2006.01)
*A61L 31/18* (2006.01)
*A61B 19/00* (2006.01)

(52) U.S. Cl.
CPC ............... *A61L 31/18* (2013.01); *A61B 19/54* (2013.01); *A61B 2019/446* (2013.01); *A61B 19/44* (2013.01); *A61B 2019/5437* (2013.01)
USPC .......................................... 600/431; 600/395

(58) Field of Classification Search
None
See application file for complete search history.

(56) References Cited

U.S. PATENT DOCUMENTS

| 4,793,635 | A | * | 12/1988 | Lovison | 283/74 |
| 4,863,470 | A | * | 9/1989 | Carter | 623/8 |
| 5,044,955 | A | * | 9/1991 | Jagmin | 433/229 |
| 5,081,997 | A | * | 1/1992 | Bosley et al. | 600/458 |
| 5,431,695 | A | * | 7/1995 | Wiklund et al. | 607/36 |
| 5,509,805 | A | * | 4/1996 | Jagmin | 433/215 |
| 5,827,215 | A | * | 10/1998 | Yoon | 604/15 |
| 6,277,089 | B1 | * | 8/2001 | Yoon | 604/1 |
| 6,324,428 | B1 | | 11/2001 | Weinberg et al. | |
| 6,333,970 | B1 | * | 12/2001 | LeMaitre et al. | 378/162 |
| 6,685,452 | B2 | | 2/2004 | Christiansen et al. | |

(Continued)

FOREIGN PATENT DOCUMENTS

EP      1795226 A1    6/2007

OTHER PUBLICATIONS

PCT International Search Report and Written Opinion dated Feb. 29, 2012 related to U.S. Appl No. 12/882,786.

*Primary Examiner* — Nicholas Evoy
(74) *Attorney, Agent, or Firm* — Mueting, Raasch & Gebhardt, P.A.

(57) ABSTRACT

A radiopaque marker for inclusion within an implantable medical device (IMD) may comprise one or more radiopaque articles selected from a predetermined set of radiopaque articles. The one or more radiopaque articles may be carried by an object formed of or including, a desiccant. The predetermined set of radiopaque articles may undergo a single qualification process that approves the use of any combination of one or more of the articles as a radiopaque marker within an IMD. This allows a potentially-limitless number of markers to be made available based on a single qualification process. The radiopaque marker may serve to provide information such as the make, model, and feature set of the device.

18 Claims, 12 Drawing Sheets

(56) References Cited

U.S. PATENT DOCUMENTS

| | | | |
|---|---|---|---|
| 7,678,100 B2* | 3/2010 | Chin et al. | 604/533 |
| 7,785,302 B2* | 8/2010 | Powers | 604/288.02 |
| 7,881,796 B2 | 2/2011 | Scott et al. | |
| D661,398 S* | 6/2012 | Dutschmann | D24/158 |
| 8,202,259 B2* | 6/2012 | Evans et al. | 604/288.02 |
| 8,257,325 B2* | 9/2012 | Schweikert et al. | 604/288.01 |
| 2001/0025155 A1* | 9/2001 | Yoon | 604/1 |
| 2002/0161354 A1* | 10/2002 | Christiansen et al. | 604/892.1 |
| 2004/0186377 A1* | 9/2004 | Zhong et al. | 600/431 |
| 2005/0112758 A1* | 5/2005 | Archambault et al. | 435/307.1 |
| 2005/0278023 A1* | 12/2005 | Zwirkoski | 623/11.11 |
| 2007/0055359 A1* | 3/2007 | Messer et al. | 623/1.34 |
| 2008/0065191 A1* | 3/2008 | Bolduc et al. | 623/1.14 |
| 2009/0171274 A1* | 7/2009 | Harley et al. | 604/95.04 |
| 2009/0318994 A1* | 12/2009 | Eidenschink et al. | 607/10 |
| 2010/0069743 A1* | 3/2010 | Sheetz et al. | 600/424 |
| 2010/0200778 A1* | 8/2010 | Drobnik et al. | 250/506.1 |
| 2011/0054235 A1* | 3/2011 | Drobnik et al. | 600/8 |
| 2011/0172718 A1* | 7/2011 | Felix et al. | 606/305 |
| 2012/0065500 A1* | 3/2012 | Rogers et al. | 600/431 |
| 2012/0065503 A1* | 3/2012 | Rogers et al. | 600/431 |

* cited by examiner

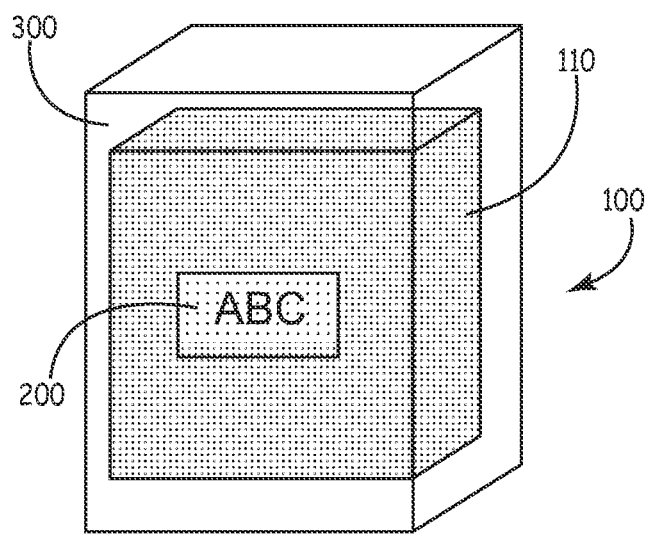
FIG. 3
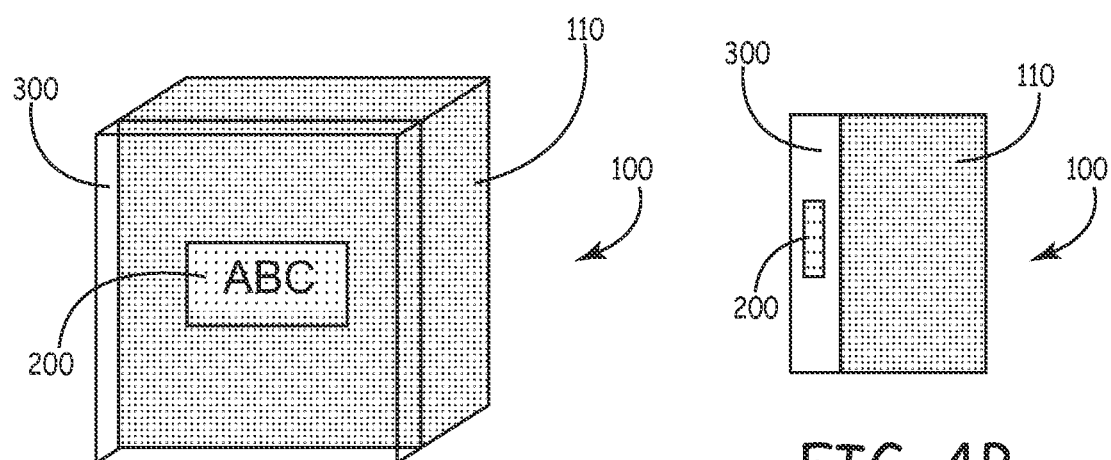
FIG. 4A
FIG. 4B

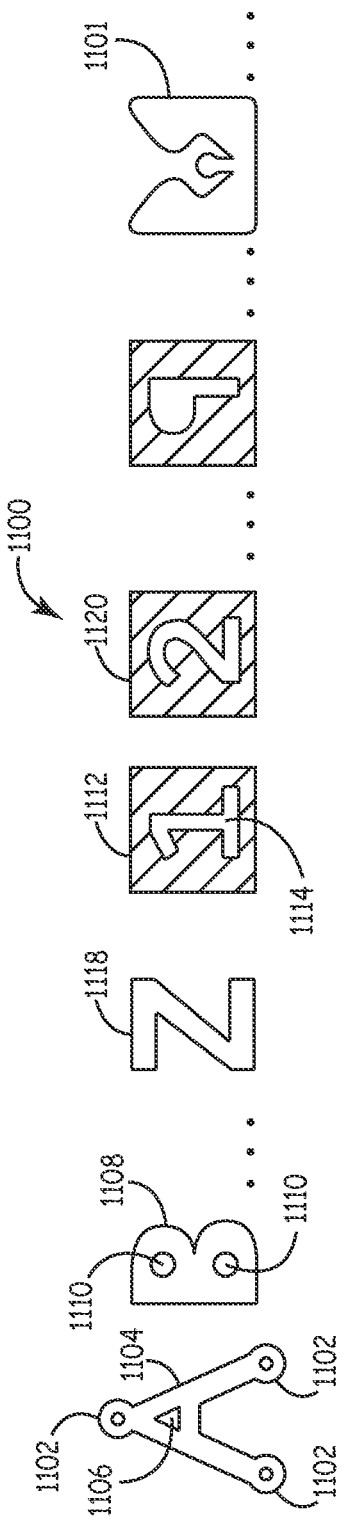
FIG. 12
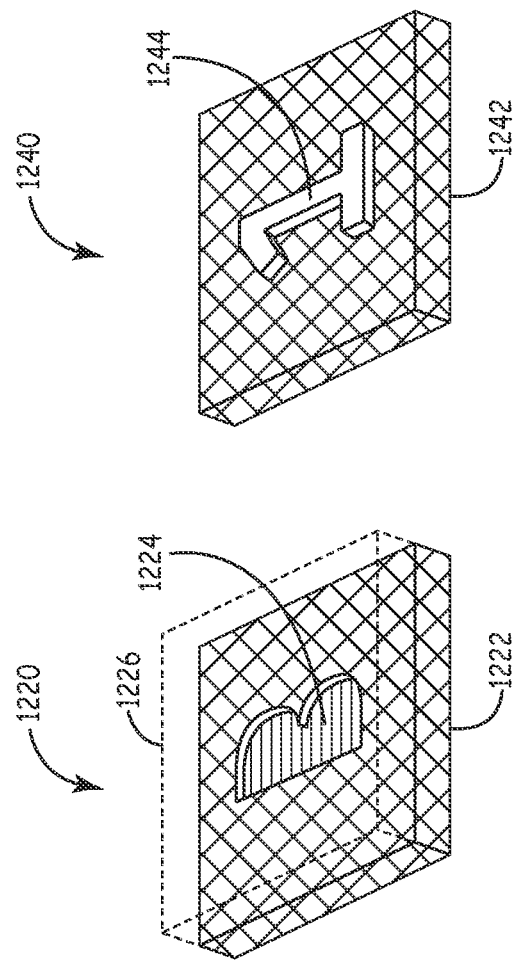
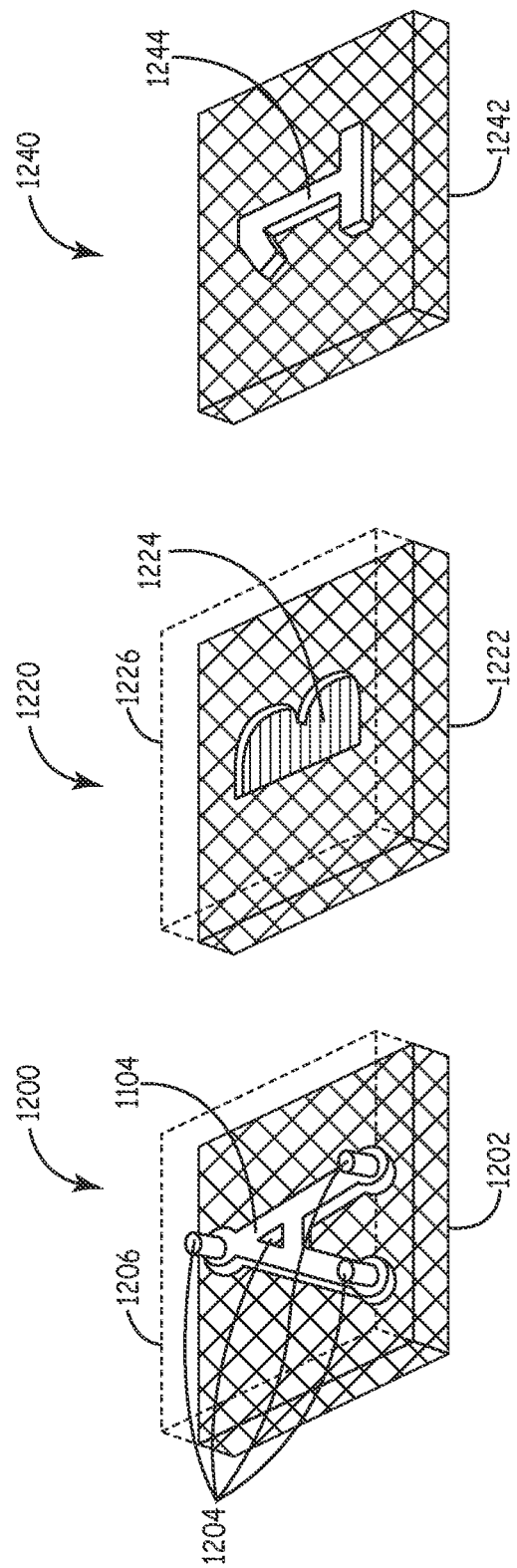
FIG. 13A  FIG. 13B  FIG. 13C

RADIOPAQUE MARKERS FOR IMPLANTABLE MEDICAL DEVICES

RELATED APPLICATIONS

This application is a continuation-in-part of, and claims priority to, U.S. patent application Ser. No. 12/882,786 filed Sep. 15, 2010, which is incorporated herein by reference in its entirety.

FIELD

The present disclosure relates to implantable medical devices, particularly to implantable medical devices having radiopaque markers.

BRIEF SUMMARY

The present disclosure describes, among other things, a predetermined set or collection of articles, each formed of a radiopaque material. This set of articles may include, for instance, letters, numbers, predefined or arbitrary symbols and/or any other types of characters. In one example, the complete set of articles may undergo a qualification process whereby all of the articles in the set are verified as meeting the appropriate standards and regulations for inclusion in an implantable medical device (IMD). Once so qualified, any combination of the one or more articles in the set may be used in any arrangement and combination to generate a single radiopaque marker. Because any combination of the one or more articles in the set may be used in any order or arrangement to generate a radiopaque marker, a virtually limitless number of markers may be created using the one qualified set. In this manner, one qualification process will suffice to qualify markers for a variety of implantable devices.

In some cases, the combination of one or more articles used to create the radiopaque marker may be carried by a desiccant article for placement in an IND. For example, the radiopaque marker may be adhered to, molded into, embedded within, or otherwise affixed to the molded desiccant article. The radiopaque marker may serve to provide information regarding the make and model of the device, may identify various features of the device (e.g., whether the device is MRI conditionally-safe) and/or may be used for purposes of determining whether the desiccant was placed in the device.

In other cases, the combination of one or more articles comprising the marker may be molded into, or affixed to, some other element or component of the device besides a desiccant article. For instance, the marker may be embedded into or otherwise carried by the device header, an insulator cup, a circuit board assembly (e.g., a flex circuit), a surface of the can of the device, or any other element of the device. In one instance, the one or more individual articles comprising the marker are held in place by an adhesive tape. This tape may be tape that also holds a circuit board assembly in position. For example, the tape that so retains the circuit board may be provided with a tab adapted to affix to the one or more articles of the marker. Alternatively, the articles may be carried by layers of a flex circuit board.

In another example, the one or more articles selected from the set of articles are arranged in a predetermined orientation relative to one another and this arrangement is maintained by a marker object. For instance, this marker object may be formed of a polymer or another material in which the one or more articles are embedded or otherwise carried. This marker object may then be affixed to, or otherwise carried by, another object of the IMD, such as a header block or core cup assembly. By using pre-assembled marker objects, the assembly of the implantable device may be simplified, since the individual radiopaque objects, which may be very small, need not be handled during final assembly of the device.

In one embodiment, an IMD is disclosed that comprises a radiopaque marker comprising multiple radiopaque articles arranged in a predetermined manner and an object adapted to carry the radiopaque marker. The radiopaque articles may be selected from a predetermined set of radiopaque articles, each of the radiopaque articles in the set having at least one characteristic in common with all other radiopaque articles in the set. For example, the characteristic may be a physical dimension. The radiopaque articles may comprise alphanumeric characters and/or arbitrary symbols formed of radiopaque material. The radiopaque articles may indicate one or more of a manufacturer, a type of the IMD, a model of the IMD, features of the IMD, a date associated with the IMD, and a location associated with the IMD. Such articles may be formed of an radiopaque material such as tungsten, Hastelloy®, titanium, or any other suitable radiopaque material.

In one example, the object adapted to carry the radiopaque marker is formed of a desiccant and/or a polymer. The object adapted to carry the radiopaque marker may be a flex circuit, a cup assembly, or the housing of the IMD, or any other component that serves a purpose within the IMD beyond providing the marker function. Alternatively, the Object may be a marker object that is specifically adapted to retain the one or more articles selected for inclusion in the marker in a predetermined arrangement to one another without serving another purpose beyond the marker function.

The object adapted to carry the radiopaque marker may comprise one or more features adapted to retain the radiopaque articles in a predetermined arrangement. Alternatively or additionally, the radiopaque articles themselves may comprise features adapted to retain the radiopaque articles with respect to the object adapted to carry the radiopaque marker. In a specific example, the one or more features of the object may be adapted to mate with one or more features of the radiopaque articles to retain the radiopaque articles in position.

Another example of the disclosure involves a method comprising selecting one or more radiopaque articles from a predetermined set of multiple radiopaque articles and carrying the one or more radiopaque articles as radiopaque marker within an implantable medical device (IMD). Each of the predetermined set of multiple radiopaque articles may have an attribute in common with the other radiopaque articles in the set. For example, the attribute may be a physical dimension or a feature that is provided for use in retaining the radiopaque article in a predetermined arrangement within the IMD (e.g., a tab containing an aperture). The predetermined set of multiple radiopaque articles may include one or more alphanumeric or other characters, predefined symbols and/or arbitrary symbols. Some articles in the set may be adapted to provide a positive image when detected by imaging technology. Other articles in the set may be designed to project a negative image when viewed by imaging technology.

The method may further comprise providing an object adapted to carry the one or more radiopaque articles and/or arranging the one or more radiopaque articles in a fixed relationship relative to one another. For example, the radiopaque articles may be arranged in a two- or three-dimensional arrangement relative to one another. At least one of the fixed relationship and the selected one or inure articles may convey information related to the IMD.

Carrying the one or more radiopaque articles may comprise embedding the one or more radiopaque articles within a desiccant article or polymer article carried by the IMD and/or affixing the one or more radiopaque articles with an adhesive or a tape. The method may further comprise requiring the predetermined set of multiple radiopaque articles to undergo a qualification process to allow any combination of the multiple radiopaque articles to be selected for inclusion in the IMD.

In another example, a radiopaque marker for an implantable medical device is disclosed that comprises multiple radiopaque articles arranged in a predetermined manner and a marker object adapted to carry the multiple radiopaque articles in the predetermined manner.

Other aspects of the disclosure will become apparent to those skilled in the art from the drawings and the associated description.

BRIEF DESCRIPTION OF THE DRAWINGS

FIGS. 1-3 and 4A are schematic perspective views of embodiments of molded desiccant articles with an affixed radiopaque marker.

FIG. 4B is a schematic side view of an embodiment of the article depicted in FIG. 4A.

FIG. 12 is a diagram illustrating a set of radiopaque articles that may be used to create a radiopaque marker in one example of this disclosure.

FIG. 13A-13F are perspective views of portions of objects that are adapted for carrying one or more radiopaque articles that may be selected from a set of such articles.

Figure 1:
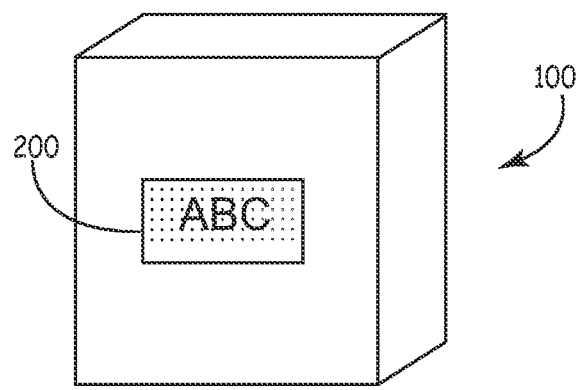

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

Implantable medical devices may include a radiopaque marker for purposes of identifying the device manufacturer and model. Such device identification markers are x-ray visible and are distinguishable from other components of the device. The identification markers are valuable in emergency situations to allow a physician or other health care provider to determine whether a patient has an implanted device, and if so, the make and model of the device, and whether any special precautions may be needed in treating the patient in the emergency situation in light of the implanted device.

Markers may convey information in several ways. For instance, a shape included as part of the marker may be defined, in part, by "cutaway" portions of radiopaque material. As a specific example, a manufacturer's logo may be cut out of an otherwise continuous surface of radiopaque material so that an image of this cutaway portion can be used to determine the manufacturer of the product. Other cutaway shapes may provide an indication as to the model of the device, and so on.

When imaging technology is used to view such a marker, the cutaway portions appear as a "negative" image of the information to be conveyed. That is, it is the absence of portions of the radiopaque material (i.e., the "cutaway" portions) rather than the presence of such material, which serves to convey information. In some cases, determining the exact shape of a cutaway portion can be challenging, particularly when the radiopaque marker is small.

Another consideration associated with use of radiopaque markers involves the manufacturing qualification process a marker must undergo before it can be included in an IMD. Each component contained within an IMD, including radiopaque markers, must undergo a respective qualification process to ensure that the component is safe and can be reliably re-produced and inspected. This process is expensive and time-consuming. It is therefore desirable to reduce costs associated with qualifying radiopaque markers.

Still another challenge associated with the use of radiopaque markers relates to finding an appropriate location at which to place a radiopaque marker, particularly since the size of implantable medical devices has continued to shrink as technology has progressed.

Aspects of the current disclosure address the foregoing and other challenges associated with use of radiopaque markers within implantable devices. According to this disclosure, various components of the IMD may be adapted to carry a radiopaque marker. For instance, the marker may be affixed to, or otherwise carried by, a portion of the inside of a housing of the device. The marker may be held in position by an acrylic adhesive tape, a pressure sensitive adhesive (PSA), or any other suitable mechanism for affixing the marker to a desired location. As another example, an insulating core cup assembly or header block of the device may be adapted to carry the marker. In this case, the marker may be embedded within a polymer insulator cup or header block, for instance. As yet another illustration, the marker may be embedded within or otherwise carried by a circuit board assembly which may optionally utilize flex technology. As still another illustration, the marker may be held in place or affixed to tape that holds a flex circuit or some other component of the implantable device in place.

In still other examples, as implantable devices continue to shrink in size, the foregoing approaches for positioning the marker may not be possible. In such examples, it may be more practical to include the marker within a desiccant contained within the device. For example, the marker may be molded within a desiccant article.

In this disclosure, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to." it will be understood that the terms "consisting of" and "consisting essentially of" are subsumed in the term "comprising." For example, a microfluidic device comprising a sheet having an interconnected microporous structure, a double-sided adhesive layer, and film may consist of, or consist essentially of, the sheet, the adhesive layer and the film.

"Consisting essentially of", as it relates to compositions, articles, systems, apparatuses or methods, means that the compositions, articles, systems, apparatuses or methods include only the recited components or steps of the compositions, articles, systems, apparatuses or methods and, optionally, other components or steps that do not materially affect the basic and novel properties of the compositions, articles, systems, apparatuses or methods.

Any direction referred to herein, such as "top," "bottom," "left," "right," "upper," "lower," "above," below," and other directions and orientations are described herein for clarity in reference to the figures and are not to be limiting of an actual device or system or use of the device or system. Devices or systems as described herein may be used in a number of directions and orientations.

The present disclosure describes, among other aspects, a radiopaque marker for inclusion in an implantable medical device. The radiopaque marker may be carried or otherwise affixed to an object so that it can be used to provide information associated with the implantable medical device when imaging systems such as X-ray technology is employed in conjunction with the device.

As previously discussed, one challenge associated with use of radiopaque markers is finding an appropriate carrier for the marker, particularly as device sizes become ever smaller. In one example, the object on which the radiopaque marker is carried may be a molded desiccant article for placement in an IMD. The radiopaque marker may be affixed to the molded desiccant article in any suitable manner. For example, the radiopaque marker may be incorporated into the molded desiccant article, impregnated in the article, adhered to the article, embedded in the article, molded in the article or the like. The radiopaque marker may serve to provide information regarding the make and model of the device, a type of the IMD, features associated with the IMD, a date and/or location (e.g., date and/or location of manufacture) associated with the IMD, and/or to indicate whether the desiccant was placed in the device.

in one example, the molded desiccant article may be formed of one or more individual cutout radiopaque articles such as characters or symbols arranged in a predetermined manner such as in a character string. The one or more individual articles may be alphanumeric characters and/or any other symbols that are included as part of a set of articles that is qualified in a single qualification process. This qualification process is performed to ensure that any of the set of radiopaque articles is safe for inclusion in an implantable device, as will be described in detail below.

The molded desiccant article and the associated radiopaque marker carried by that article may be used in any suitable implantable medical device. For example, devices having a component that may corrode, short-circuit, or exhibit performance shifts in the presence of moisture may desirably include a desiccant article as described herein. Often, such devices include an electrical component. Examples of such devices include hearing implants, cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators, infusion devices, and the like.

Any one or more suitable desiccants may be used in a molded desiccant article. Examples of desiccants that may be employed, include calcium oxide, silica gel, activated carbon, activated alumina, clay, other natural zeolites, anhydrous magnesium, calcium sulfate, starches, molecular sieves, aluminosilicates, and the like. In an embodiment, the desiccant may comprise aluminum and/or calcium oxide.

The desiccant used may be molded by combining with any suitable polymeric material. Thermoplastic polymers, including, but not limited to, polyolefins, polyethylenes, polystyrenes and polypropylenes, may readily be used in forming a molded desiccant article. Thermoset polymers, such as silicones, styrene-butadiene polymers, and the like may also be used.

The desiccant and the polymer may be blended, mixed, or the like, prior to molding so that the desiccant is embedded in the polymer. Any suitable amount of polymer and desiccant may be used. For example, a mixture of desiccant and polymer for purposes of molding may have about 5 to about 60 weight percent desiccant and about 95 to about 40 weight percent polymer. In some embodiments, such a mixture includes about 25 to about 50 weight percent, such as between about 40 and about 50 wt %, desiccant. In some embodiments, such a mixture may include about 50 to 75 weight percent, such as between about 50 and about 60 wt %, polymer. If more than one desiccant or polymer is used, the weight percent of the polymer will be the cumulative weight percent of all of the polymers and the weight percent of the desiccant will be the cumulative weight percent of all of the desiccants.

In many cases, the mixture of desiccant and polymer will consist of, or consist essentially of, desiccant and polymer. However, in some cases one or more additives, such as a compatibilzing or coupling agent may be added as well. Such agents are generally known in the art and generally make up 5% or less of the weight of the mixture.

Any radiopaque material may be used in forming a radiopaque marker. Such materials are known in the art. In some embodiments, gold, platinum, platinum/iridium, titanium, tantalum, barium silicate or tungsten are used in forming the radiopaque marker. Of course, other materials may be used. Preferably, the marker is readily discernable from other materials of a device in which the marker is placed. For example, if the device includes components formed from titanium, it may be desirable for the marker to be formed from a radiopaque material other than titanium, such as tungsten.

The radiopaque marker may be affixed to the molded desiccant article in any suitable manner. For example, the radiopaque marker may be incorporated into the molded desiccant article, impregnated in the article, adhered to the article, embedded in the article, molded in the article or the like. In some cases, the radiopaque marker is a dye or fine material that is mixed with the polymer and desiccant prior to molding. In such cases, the radiopaque marker may not readily serve as a valuable indicia of an attribute of the device. In some embodiments, the radiopaque marker serves as an indicia of an attribute of the device, such as a capability of the device, the device manufacturer, or the device model. A predetermined arrangement of numbers, letters, and/or symbols may be used to serve as the indicia. In such cases, the marker may be a sheet, plate, disc, or the like with the numbers, letters, or symbols cut or punched out. In this case, the information conveyed by the marker is provided by the outline of the "cutaway", or punched out, portion. Thus, the information may be described as a negative image since the portion of the radiopaque material that is absent is the portion that is being used to convey the information.

In other examples, the marker may include one or more of the cut or punched out letters, numbers, or symbols. For instance, the marker may comprise one or more radiopaque articles selected from a predetermined set of radiopaque articles. Each such radiopaque article in the set may be a respective alphanumeric character or other symbol. The radiopaque articles may be arranged in any manner to form the radiopaque marker. The radiopaque articles selected for inclusion within the marker may be used to convey information associated with the implanted device. In yet another example, the specific combination of articles may be used to convey information. Further, the arrangement of the articles in the marker may be used to convey information about the device. As an example, the ordering of the characters within a sequential list or a two- or three-dimensional array may be used to convey information. For instance, radiopaque article residing at a first predetermined position within the marker may be defined as identifying a make of the device, another radiopaque article residing at another position may be defined as conveying information about the model of the device, and so on.

In an embodiment wherein cut out or punched out articles are used in the marker, the radiopaque articles provide a "filled in" shape that conveys the information. The marker is therefore said to be a "positive" (rather than a "negative", or cutaway) image. In some instances, particularly when the marker is relatively small in size, this type of positive image is more readily discernible using imaging technology than is a negative, or "cutaway", image. This is discussed further below.

When the marker serves as indicia, the marker should be of sufficient size to be detectable as the indicia, but is also preferably small enough so as to not take up much space in the device or the molded desiccant article. In various embodiments, the radiopaque marker has a thickness of 0.01 inches or less, such as about 0.008 inches. The marker may have any suitable length and width. In various embodiments, the marker has a length of 0.5 inches or less and a width of 0.5 inches or less. In one example, the length may be about 0.2 inches and the width may be about 0.15 inches. In yet another embodiment, the radiopaque marker may have a length and width of about 0.14 inches and 0.06 inches, respectively.

Figure 2:
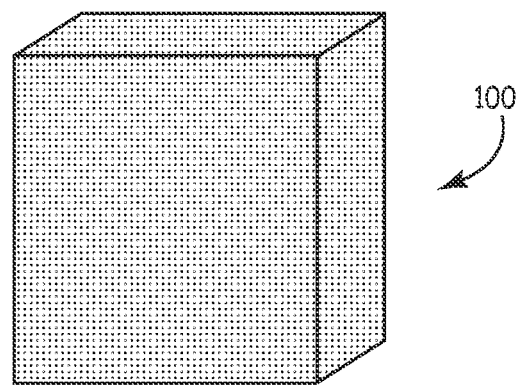

Referring now to FIG. 1, in this example, a molded desiccant article 100 is provided as an object which carries radiopaque marker 200. The marker 200 may be affixed to the article 100 in any suitable manner and at any suitable depth. In many cases, a molded desiccant having a desiccant and a polymer is visually opaque due to the presence of the desiccant. Thus, if the radiopaque marker 200 is positioned too far below a surface of the molded article 100, the marker 200 may not be visible. For example, see FIG. 2 in which the marker is embedded too far below the surface of the article 100 to be seen. The marker 200 may be affixed to the article 100 in either manner, i.e., so that it can be visually detected or so that it cannot be seen. In some cases, it may be desirable for the marker to be visible so that the presence of the marker in the molded desiccant article can be verified prior to placement in an IMD before final assembly of the device. In some cases, it may be desirable to have the marker 200 embedded with the article 100 at a depth where it cannot be seen to ensure that the marker 100 remains affixed to (e.g. embedded in) the article 100.

While the desiccant article 100 is referred to herein as a molded article it will be understood that the desiccant article may be formed in any suitable manner, such as extrusion, provided that it includes a polymeric material and a desiccant.

In the example of FIG. 1, marker 200 includes multiple individual radiopaque articles shown as "A", "B", and "C". More or fewer such radiopaque articles may be included in marker 200. In this example, these articles are shown arranged in a character string. In another example, radiopaque marker 200 may have the individual radiopaque articles arranged in another manner, such as in a two-dimensional array of characters or in some other two-dimensional pattern. In another example, the radiopaque marker may comprise a three-dimensional arrangement of radiopaque articles such that not all of the radiopaque articles are aligned, on a same plane as all other markers. This may be useful in allowing the marker to be viewed from multiple angles, as when the IMD is in various positions or orientations relative to an imaging device. In one embodiment, the marker may include multiple instances of a set of articles, with each set of articles being arranged in a different plane to make information viewable from multiple directions.

As discussed above, the position occupied by a particular radiopaque article may assign significance to that radiopaque article. For instance, a first one or more radiopaque articles in a sequential string of articles (e.g., article "A") may be designated to denote a make of the device. A second one or more radiopaque articles in a sequential string of articles may denote a feature set of the device, and so on. In the case wherein a two- or three-dimensional array or other pattern is used to form the marker, the position of an article within the array or other pattern may likewise assign a particular significance to the radiopaque article. In this manner, not only the article itself, but also the position of the article, may be used to convey information associated with the implantable medical device.

In the example of FIG. 1, each of the radiopaque articles included in marker 200 is an alphabetical character. In an alternative embodiment, the marker may alternatively or additionally include numeric characters or any other types of symbols. Such symbols may be predefined (e.g., #, %, @, etc.) or may be entirely arbitrary (e.g., symbols defined by a manufacture such as a logo of a manufacturer.)

In one embodiment, each of the articles in the set of articles used to form the marker may have similar characteristics, such as being made via a common manufacturing process, being formed of a same material, having roughly a same size (e.g., length, width, and/or material thickness), having similar feature(s) used to affix or retain a position and/or orientation of the article, and so on. Having common characteristics (e.g., size) may allow a selected combination of the articles to be more readily incorporated within a same marker.

The symbols in the example of FIG. 1 may be said to provide a "positive" outline of the information to be conveyed. As described above, this means that the radiopaque material forms the actual cutout characters. As a specific illustration, the characters "A", "B", and "C" of this example are cut out of, or otherwise formed from, a radiopaque material. The remainder of marker 200 (that is, the object that carries the radiopaque articles) may be formed of a non-radiopaque material such as a polymer. This positive image of the information is in contrast to a negative image wherein portions of a radiopaque material are cutaway to provide information. As a specific example, the letters "A", "B", and "C" may be cut out of a sheet of radiopaque material so that when imaging technology is used to view marker 200, this cutaway image is visible. This is akin to shining a light through a window into a dark room such that the outline of the window may be visible on an adjacent wall. While either type of image is contemplated herein in various embodiments, the use of a positive image of the type shown in FIG. 1 may provide a marker 200 that is more readily discernibly, particularly when the marker is relatively small.

Figure 5:
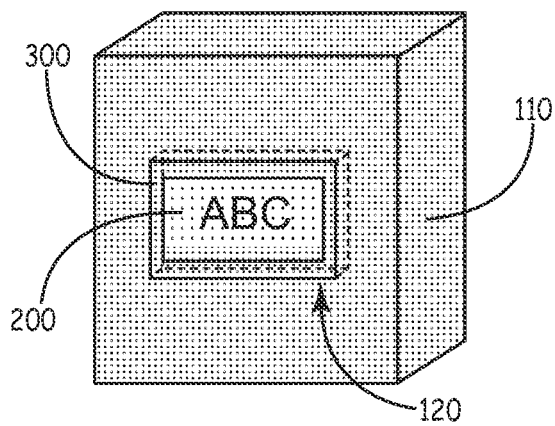
FIGS. 5-6 are schematic perspective views of embodiments of molded. desiccant articles with an affixed radiopaque marker.

Referring now to FIGS. 3-5, embodiments of a molded desiccant article 100 having an affixed radiopaque marker 200 and an over-molded optically transparent polymer 300 are shown. As used herein, "optically transparent" means that an object lying beyond a body can be clearly seen through the body. In the depicted embodiments, a molded part 110 is provided as the object which carries radiopaque marker 200. This molded part 110 may include a desiccant and a polymer that may optionally be optically opaque. The over-molded polymer 300 may be optically transparent, allowing visualization of the radiopaque marker 200. The marker is at least partially embedded in the over-molded polymer 300. With reference to FIG. 3, the over-molded polymer 300 is molded about the entire surface of molded part 110.

In FIGS. 4A-B, the over-molded polymer 300 is molded over one face of molded part 110. As shown in FIG. 4B, which is a side view of an embodiment of the article 100 depicted in FIG. 4A, the radiopaque marker 200 may be embedded in the over-molded polymer and not molded part 110. This allows the radiopaque marker 200 to be visually observed through the optically transparent over-molded polymer 300. The over-molded polymer 300 not only serves as a window for viewing the marker 200 but also serves to affix the marker 200 to the article 100. While not shown, it will be understood that the marker 200 may be partially embedded, or fully embedded at a shallow depth, in the molded part and may still be visible. The over-molded polymer 300 can serve to aid in the retention of the marker 200 in the article 100. It will be understood that the over-molded polymer 300 should not substantially interfere with the ability of the desiccant to sequester moisture. If the over-molded polymer 300 is formed from material, or has a property (e.g. thickness), that may interfere with the desiccant; the amount of surface area of article 100 that the over-molded polymer 300 covers may be limited to prevent substantial interference with the desiccant. The thickness of the polymer may be minimized to prevent substantial interference with the desiccant or the like.

Referring now to FIG. 5, the molded part 110 may have a recess 120 into which the marker 200 fits. The over-molded optically transparent polymer 300 fills the recess 120 and aids in the retention of the marker 200. Any suitable optically transparent polymer may be used as the over-molded polymer 300 depicted in FIG. 2-5. In many embodiments, the polymer is the same as the polymer employed in the molded part that includes the desiccant. The absence of the desiccant may render the polymer optically transparent so that a marker, 300 under, or in, the polymer can be seen.

In some embodiments, a multi-shot (e.g., two-shot) injection molding process may be employed to produce an article 100 as depicted in FIGS. 3-5. However, any other suitable process may be employed to produce an article 100 with an over-molded polymer 300 as depicted in FIGS. 3-5.

It will be understood that the embodiments depicted in FIGS. 3-5 are only some of the contemplated ways for affixing the marker 200 to the device 100 in a manner such that the marker 200 is visible and that any other suitable mechanism may be used so that the marker 200 is visible.

Figure 6:
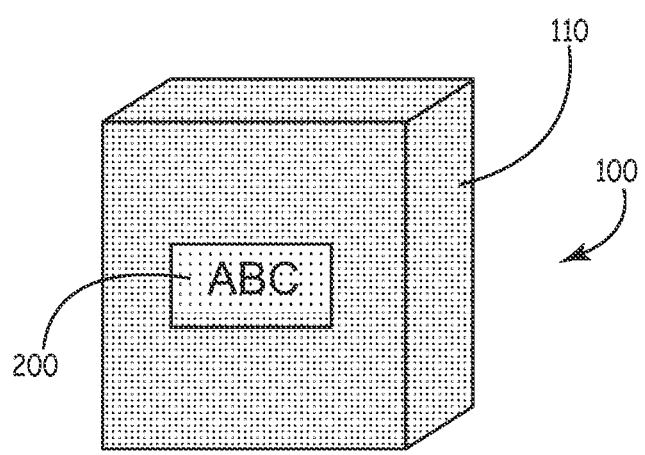

For example, and with reference to FIG. 6, the marker 200 may be partially embedded, embedded just under the surface, or adhered to the molded part 110 so that the marker 200 is visible. In many cases, it is desirable to omit added components or process steps. Thus, in some cases, it may be desirable to affix the marker 200 to the device 100 without the use of an adhesive, such as a pressure sensitive adhesive, and epoxy, of the like. Thus, it may be desirable to at least partially embed the marker 200 in the molded part 110 to affix the marker 200 to the device 100. Any suitable process may be employed to partially embed the marker 200 in, or embed the marker 200 just under the surface of, the molded part 110. For example, the marker 200 may be placed at a surface of a mold prior to filling the mold with the mixture including the desiccant and the polymer. By placing the marker at a surface of the mold, at least the portion of the marker that contacts the surface of the mold will not be embedded in the resulting molded part.

Figure 7:
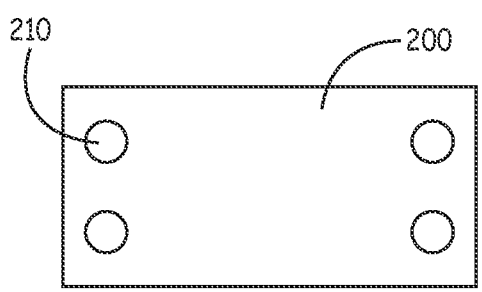
FIG. 7 is a schematic top view of an embodiment of a radiopaque marker.

Referring now to FIG. 7, the marker 200 and/or individual ones of the radiopaque articles included in the marker may comprise one or more features adapted to retain the marker or the radiopaque articles in relation to the IMD. For instance, in the current example, marker 200 includes retention holes 210 to facilitate retaining the marker 200 on a molded device. The holes are sized to allow material being molded to pass through the holes and retain the marker to the molded article. In some embodiments, one or more of the holes 210 are the indicia (e.g., numbers, letters or symbols) that are punched out of a radiopaque substrate.

Figure 8:
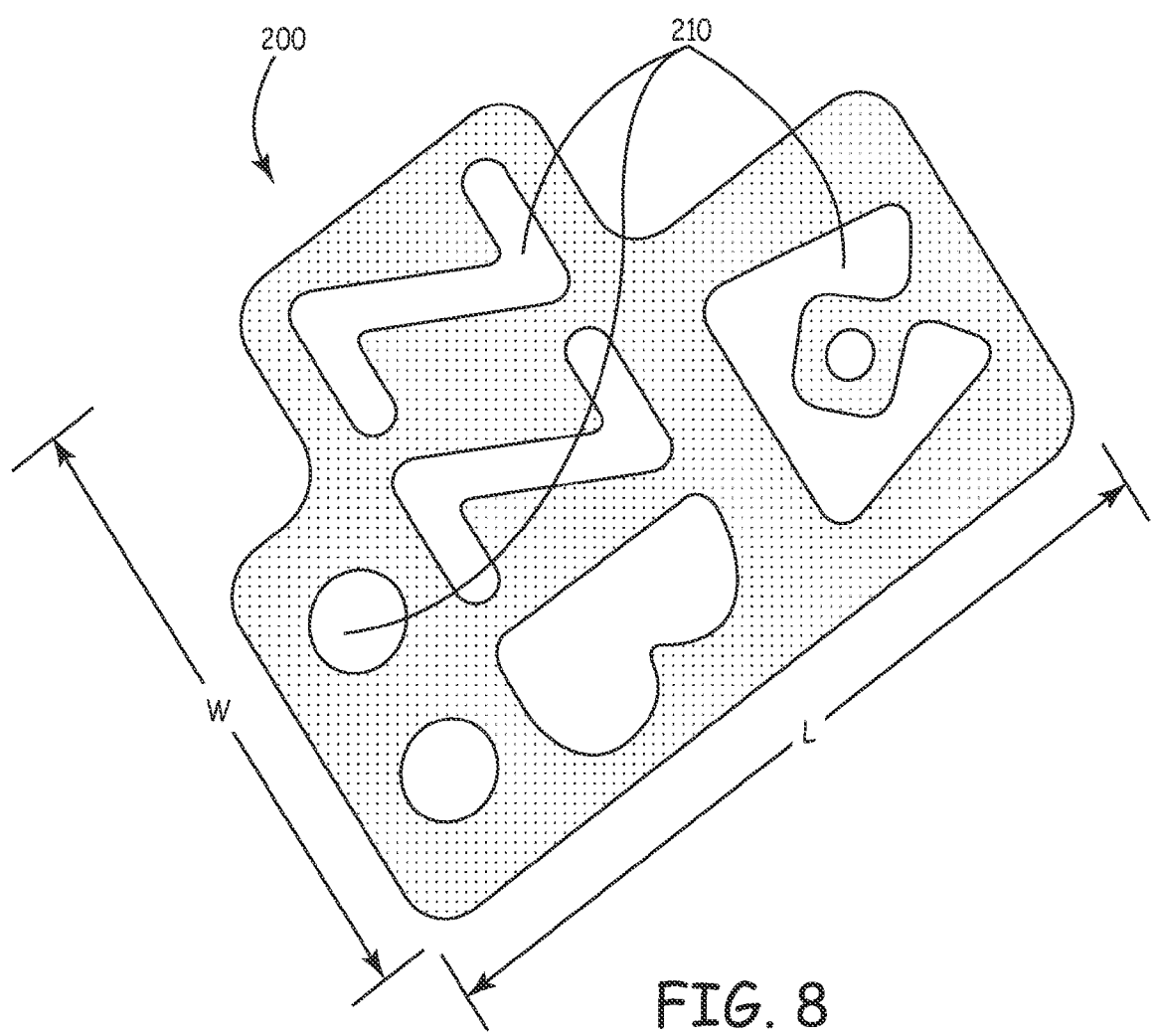
FIG. 8 is a schematic view of an embodiment of a radiopaque marker.

FIG. 8 is a schematic drawing of an example of a radiopaque marker 200 having indicia 210 (shown as "ZZB") cut out of the radiopaque material to describe one or more attributes of a device. The marker includes retention holes and the indicia also serve as retention holes. In the depicted embodiment, the marker 200 has a length L of about 0.206 inches, a width W of about 0.15 inches, and a depth of about 0.008 inches. Of course, a marker 200 may have any suitable length, width and depth and may contain any suitable indicia. For instance, alternative dimensions are given as other examples above.

FIG. 8 provides an example of a marker 200 that conveys information using a "negative" image. That is, the cutaway portions of the radiopaque material provide the information. This is opposed to conveying information using a "positive" radiopaque image, examples of which are shown in various figures including FIGS. 1, 3, 4A, 5, and 6. As previously discussed, there may be advantages to using a positive radiopaque image, such as providing more readable information, particularly when marker 200 decreases in size.

Figure 9:
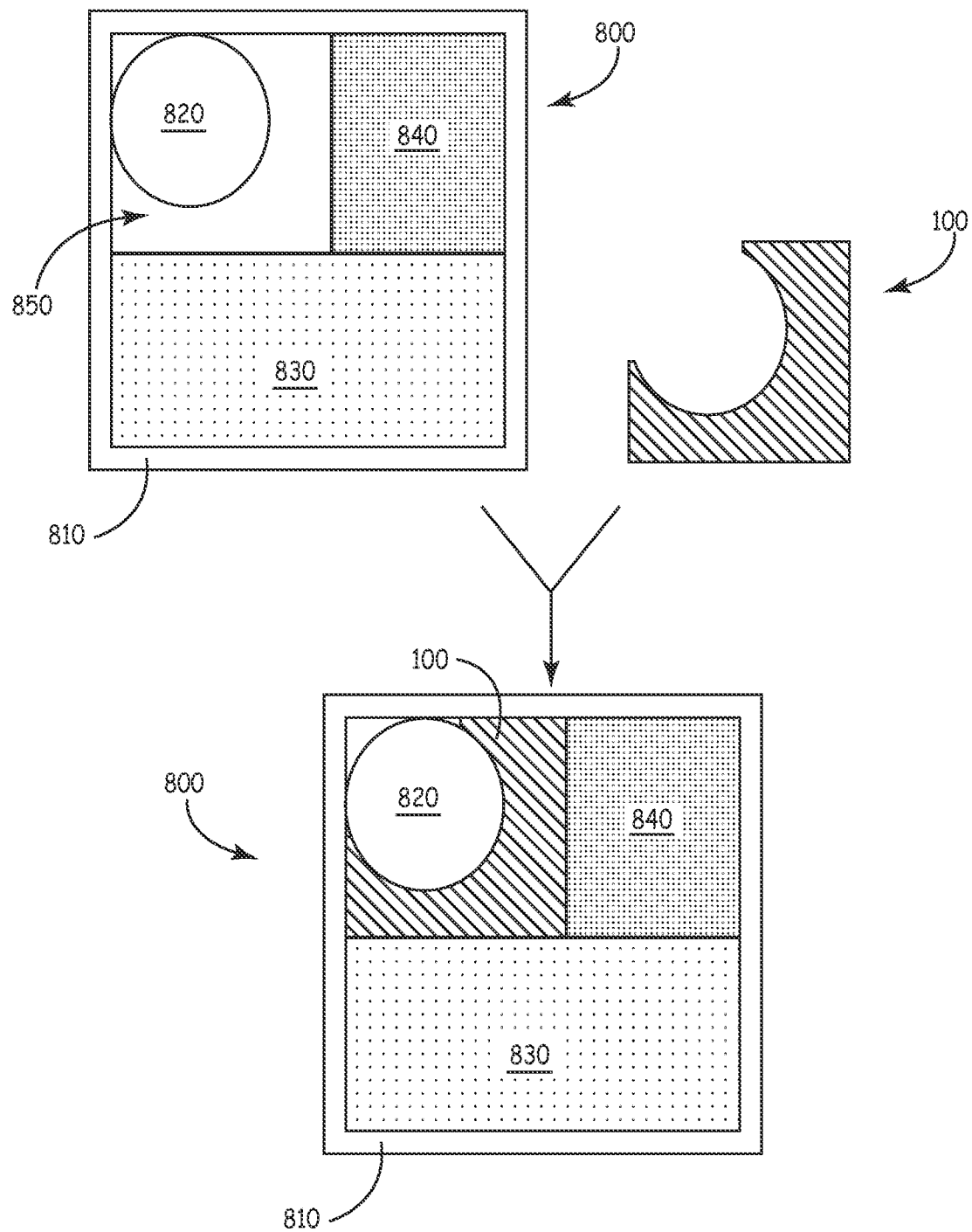
FIG. 9 is a schematic top view of embodiments of steps in the assembly of the device.

Referring now to FIG. 9, a molded desiccant article 100 having a radiopaque marker (not shown) may be placed into an implantable medical device 800. The molded article 100 is preferably formed to fill a free space 850 in the device. Depending on the design, assembly, and components of the device 800, the desiccant article 100 may be molded to occupy any suitable free space 850. Thus, the desiccant article 100 with affixed radiopaque marker can be made to fit in the device 800 without adding substantial volume to the device 800 when fully assembled.

During assembly of the device 800, one or more components 820, 830, 840 are placed within a housing 810 or a partial housing of the device. The molded desiccant article 100 may be placed in the housing 810 to occupy free space 850. The housing 810 may then be sealed to complete final assembly of the device 800. In many embodiments, at least one of the components 820, 830, 840 of the device 800 is an electronic component. The device 800 may include any electronic component, such as a microprocessor, volatile or non-volatile memory, a switch, a circuit board, a power supply, a resistor, or the like. Such components may deliver electrical stimulation to a patient and/or provide delivery of a therapeutic agent to the patent (e.g., via a pump.) The components may additionally or alternatively provide sensing capabilities to sense physiological or other signals from the patient.

Figure 10:
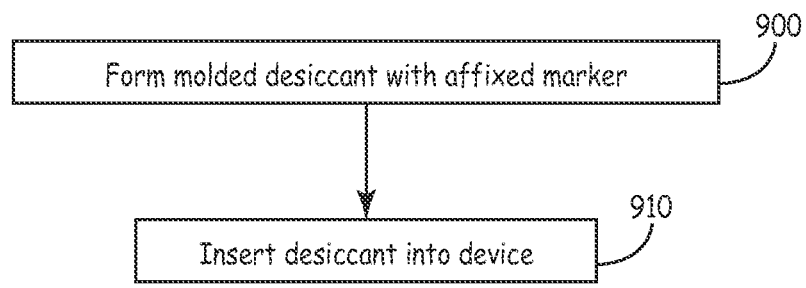
FIG. 10 is a flow diagram of a method for assembling a device having a molded desiccant article.

Referring now to FIG. 10, an overview of a method is shown. The method includes forming an object that carries the radiopaque marker. In this example, the object is a molded desiccant having an affixed radiopaque marker (900). The molded desiccant article is inserted into the device (910). The molded desiccant article can be made in any suitable manner, such as described above, and the radiopaque marker can be affixed to the article in any suitable manner, such as described above. The article may be inserted into the device at any suitable point in the assembly of the device. Typically, the molded desiccant article with an affixed radiopaque marker will be inserted near the end of the assembly process, just prior to sealing the housing.

Figure 11:
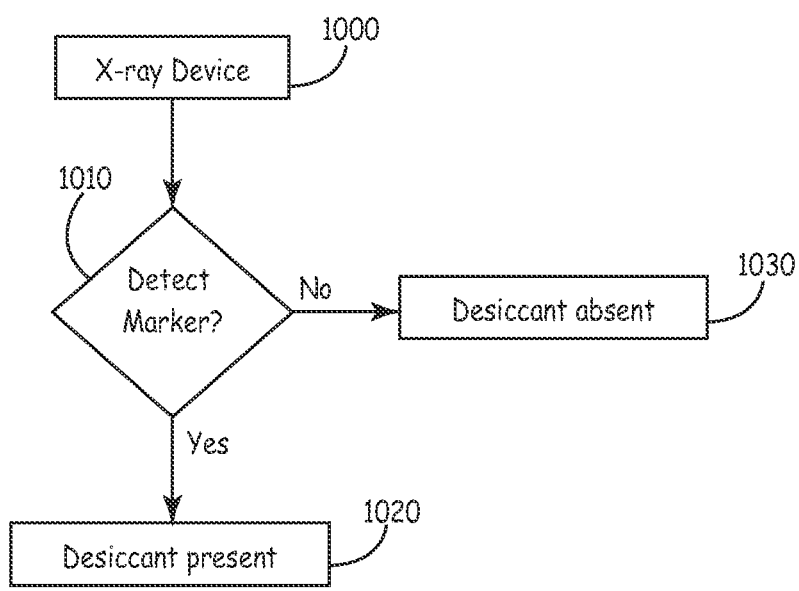
FIG. 11 is a flow diagram of a method for detecting whether a device has a desiccant according to an embodiment of the teachings presented herein.

Referring now to FIG. 11, a method for determining whether an implantable medical device contains a desiccant article is shown. The method can serve as a valuable check for a manufacturer prior to shipping the device. The device may be one that is supposed to have a molded desiccant article with an affixed radiopaque marker. The method includes x-raying the device suspected of having a desiccant article with an affixed radiopaque (1000) and determining whether the x-ray indicates the presence of the radiopaque marker (1010). If the radiopaque marker is present, a determination may be made that the desiccant is present (1020). If the radiopaque marker is not present, a determination may be made that the desiccant is not present (1030).

The foregoing description provides some examples of using a marker 200 that is carried by a desiccant article. Use of the desiccant article to carry marker 200 may provide a space savings since the desiccant can be molded to fill any unused space. This space is then also used to carry the marker. In this manner, no additional space need be provided thr the marker. Moreover, once marker 200 is incorporated in any of the foregoing ways into the desiccant article, the marker is easy to handle and place within the implantable device. Handling of marker 200 as a separate component may be more difficult, especially if the size of marker has very small dimensions.

While there are advantages to including marker 200 in, or on, a desiccant article, in other examples, the marker 200 may be carried by another object. For instance, marker 200 may be embedded within or otherwise affixed to or carried by the inside of the housing, the flex circuit, the header block, the insulator cup, tape affixed to a circuit assembly (e.g., a flex circuit assembly) or any other component of the device.

As discussed above, in one example, the radiopaque marker may be formed of one or more individual cutout radiopaque articles such as characters or symbols arranged in a predetermined manner such as in a character string, an array, or some other pattern. The one or more individual articles may be part of a larger set of articles. For instance, the larger set may include radiopaque representations of all alphanumeric characters. Alternatively or additionally, the set may include other symbols, either predefined or arbitrary. As may be appreciated, each of the articles in the set includes one or more physical attributes (e.g., shape, size, etc.) that makes the article unique as compared to other articles in the set. The unique physical attributes of an article are assigned a corresponding meaning that is employed to convey information when that article is included in a marker. A marker may be created by selecting any one or more of these radiopaque articles from this predetermined set. In this manner, the choice of articles to be included in a predetermined set will convey information about the device. In some cases, a combination of selected articles may alternatively or additionally be used to convey information. For instance, multiple articles occupying a particular position within the marker may be used to convey model information, and so on.

Allowing the marker to include any of the one or more articles from a predetermined set of such articles may provide important advantages in the development cycle. As part of a quality control process that IMDs must undergo to satisfy regulatory requirements, each component included within an IMD must undergo a qualification procedure. This qualification procedure defines the necessary feature set, the manufacturing requirements, quality control considerations, the inspection process, supplier requirements, auditing considerations, documentation requirements, and other considerations related to that component. Even relatively simple components such as radiopaque markers must undergo a qualification process. The qualification process can be time-consuming and expensive, even for components such as radiopaque markers.

Each time a new radiopaque article is created for a corresponding make and model of an IMD, that unique radiopaque article must undergo a new qualification process. This is true even though a previously-used design associated with another product may be similar to the new design. As discussed above, this can be expensive and time-consuming, adding overhead to the development cycle. According to one aspect of the disclosure, a set of radiopaque articles may be qualified in one qualification process. This set may include, for instance, all alphabetical characters, numerals between 1 and 9, and other selected symbols. Such symbols could be pre-existing symbols that have a commonly-understood meaning or may be completely arbitrary symbols such as a symbol that represents a logo of a device manufacturer. This set may then undergo a single qualification process during which all of the radiopaque articles in the set are approved for use in any combination and arrangement. The predetermined set of radiopaque articles may then be used to create a virtually limitless number of radiopaque markers, each marker having already been qualified by virtue of the single qualification process that approved use of the entire set of radiopaque articles. This will eliminate any need in the future to perform any qualification processes for additional unique markers, saving a significant amount of time and money.

In one example, the qualification process may dictate that all articles in a set of radiopaque articles in the qualified set are manufactured using predetermined techniques. Various example mechanisms for forming the radiopaque articles are set forth below. The qualification process may further dictate each of the radiopaque articles in the set have one or more dimensions that fall within a certain size range. For instance, the thickness of each radiopaque article in the set may be required to be between 0.08 and 0.15 inches in thickness. Alternatively or additionally, ranges for the lengths and widths of the characters in the set may be provided. As yet another example, the qualification may dictate what types of feature(s) each article may have for use in allowing that article to be affixed or otherwise carried relative to other components in the IMD. Examples of such features will be described below. In this manner, the qualification process may specify certain physical requirements that each such radiopaque article must have to be included within the predetermined set of radiopaque articles that has been qualified.

As previously discussed, a radiopaque marker comprised of one or more articles selected from a set of such articles can convey information in a number of ways. First, each article selected for inclusion in the marker may convey information by virtue of that article's unique shape, size, and/or other physical characteristics. For example, an article formed like the letter "M" has a unique shape which may be assigned a particular meaning (e.g., "this device is MRI conditionally safe"). Similarly, an article formed in the shape of a manufacturing logo may be used to convey the manufacturer of the device. A different article assigned some arbitrary shape may be associated with a model of an IMD. In this embodiment, the ordering or other arrangement of the articles within the marker may not be very important, since each unique article included in the marker is used to convey the necessary information.

In another embodiment, the spatial relationship of articles included in the marker may be important. For instance, a marker may include a string of three articles "MM1" arranged in a string from back-to-front within the header block of a device. The first article "M" in this string may indicate the make of the device. The next article "M" in the string may indicate a model of the device, and the third article "1" in the string may identify a feature set of the device. Thus, even though two articles in the marker are the same (i.e., "M"), the articles take on a different significance based on the spatial arrangement in the marker. In yet another example, the first two characters "MM" may be assigned a certain meaning indicative of the feature set of the device. Thus, in this example, both the spatial arrangement and the articles selected for inclusion within the marker provide information associated with the implantable device.

In other embodiments, the spatial arrangement may have a two-dimensional or even a three-dimensional aspect that may also convey information in some instances. For example, a multi-shot molding process may be used to add a three-dimensional quality to a marker. A shape of the three-dimensional marker and/or locations of the articles within the three dimensions may be used to convey information.

A three-dimensional marker may be useful, for example, when the orientation of a device is unknown such that the marker is readable from various directions. In one instance, a three-dimensional marker may utilize multiple radiopaque articles to convey the same information in multiple planes. For instance, two articles "M", both of which convey the manufacturer of the device, may be arranged to lie in two substantially-perpendicular planes within the same three-dimensional marker. This may make it easier for an imaging device to read at least one of the articles when the orientation of the IMD within the patient is unknown.

According to another aspect, some, or all, of the articles in the set may be adapted to provide a positive image when imaging technology is employed to view the marker. As discussed above, this is opposed to a negative image that is projected by imaging technology when articles are formed using "cutaway" portions of a radiopaque material. Such cutaway portions may be more difficult to interpret, especially as marker sizes become increasingly smaller.

FIG. 12 is a diagram illustrating a set 1100 of radiopaque articles that may be used to create a radiopaque marker in one example of this disclosure. Such a set is shown to include alphanumeric characters as well as arbitrary symbols such as article 1101. Each article has unique physical attributes (e.g., a unique shape). When used in a marker, each article (as identified by the unique physical attributes of that article) may be associated with, or assigned, a particular meaning and/or a particular combination or arrangement of articles may be associated with a meaning.

Each article may take on any desired shape. For instance, an article of the set may have a shape selected to project a positive image (e.g., the alphabetical characters of FIG. 12 such as article 1104) when viewed with imaging technology. Other articles may be included in the set that convey a negative image (e.g., the numerical characters such as article 1112 that include "cutaway" portions (e.g., portion 1114). Of course, the set of FIG. 12 is an example only, and a set as contemplated herein may include more or fewer articles, and may include different articles instead of, or in addition to those shown.

In the example of FIG. 12, all of the articles in the set may share one or more characteristics. Examples of such characteristics may include, but are not limited to, height, width, thickness, weight, volume of the material included in an article, the type of material from which the article is formed, and so on. Such characteristics may be determined by a qualification process. For instance, the qualification process may specify that each article in the set must have a length, width and thickness that are within predetermined ranges.

The qualification process may alternatively or additionally require each article to meet other constraints. For instance, such a process may dictate that each article in the set contains at least one feature such as tab 1102 of article 1104. As discussed above, such a tab may be used to hold article 1104 in place relative to a marker or another component of the IMD.

As still another example, the qualification may dictate that each article is to be formed according to a predetermined process that will result in certain physical characteristics. For instance, the qualification process may indicate that all articles are to be formed by a sintering process that will yield radiopaque articles that each have a certain degree of porosity, a similar type of surface, a similar variability with respect to the thickness of different portions of a given article, and so on.

As discussed above, any one or more of the radiopaque articles in a predetermined set may be combined to create a marker. The radiopaque articles of a marker may be carried directly by an object of the IMD that has a function beyond providing marker information. That is, the radiopaque articles may be embedded within, attached to, or otherwise carried by, an object that is a component of the IMD without first being affixed to one another. As a specific example, one or more radiopaque articles that have been selected to form a marker may be arranged on an inner surface of a portion of the can. An over-molded polymer layer may be applied over these radiopaque articles of the marker to affix the marker to this surface. This over-molded polymer layer may, but need not, be optically transparent so that a visual inspection may be used to confirm the inclusion of the proper marker within the device.

Alternatively, the radiopaque articles selected for the marker may be first affixed to one another to form a "marker object". This marker object serves the purpose of retaining the radiopaque articles in a certain arrangement with respect to one another. For instance, the articles may be embedded in a small polymer component. This marker object may, in turn, be affixed to or incorporated within another object of the (MD that has some other purpose beyond providing the marker function. For instance, the radiopaque articles may be embedded within polymer material during a one- or multi-shot molding process to form a marker object, and the resulting marker object may then be embedded within another polymer object (e.g., an insulator core cup assembly or header block of the IMD) during a subsequent molding process that forms that core cup assembly.

As was the case described above with respect to radiopaque articles embedded or carried by desiccant objects, the presence of the radiopaque articles that are contained on or in a different component of the IMD may be used to verify that this component has not been inadvertently omitted from the IMD. As a particular example, it may be desirable to include polymer spacers within an IMD to position and retain other components in proper spatial relationship relative to one another. It may be possible to inadvertently omit such spacers such that positioning of some components may not be as secure as would otherwise be the case. To ensure such spacers are present (even after sealing of the can of the IMD), imaging technology may be used to detect the radiopaque article(s carried by the spacers. In this manner, the marker may convey information as well as indicate the presence of another component of the system.

In some cases, one or more radiopaque articles in the set may include one or more features that are adapted to retain the radiopaque articles in a predetermined arrangement within the IMD. For instance, article 1104 may include one or more features that will mate with a corresponding feature of the object that carries article 1104. As a specific example, tabs 1102 are provided for article 1104. The tabs have apertures that can be designed to fit over posts provided in an object that is going to carry the article. Alternatively, the apertures can be used to receive a molding material that will harden to retain the article in a desired position as described in reference to FIG. 8 above.

Many mechanisms are available for carrying radiopaque articles of the type included in the set of 1100. For example, FIG. 13A illustrates a portion 1200 of an object that is designed to carry one of the articles of set 1100. Portion 1200 may be part of a marker object that will then be affixed to, or otherwise carried by, some other component of the implantable device. Alternatively, portion 1200 may be part of another component of the IMD, such as a portion of a core cup assembly, header block, a circuit board substrate, or some other component of the IMD.

In one scenario, portion 1200 may be formed in a multi-shot molding process. A first shot of material 1202 (shown with hash marks) may be applied to a mold. The resulting structure formed from the first shot of material 1202 may have features that are adapted to mate with, or otherwise interact with, a complementary feature of one of radiopaque articles from set 1100. For instance, the first shot 1202 of material may be formed to include posts 1204 or other appendages that extend from a surface to mate with tabs 1102, and optionally, the opening 1106, of article 1104. This mating of posts 1204 with tabs 1102 and opening 1106 will retain article 1104 in position while a second shot 1206 of material (shown dashed) is applied to embed article 1104 in portion 1200.

Alternatively or additionally, other types of retaining members may be included in first shot of material, if desired. Such retaining members may include recesses within a surface of the molded material to receive members extending from the surface of the radiopaque article (e.g., recesses of object 1200 to mate with posts provided on one or more surfaces of radiopaque articles). As another example, tabs may be provided on a first shot of material under which a portion of one of radiopaque articles may be designed to slide. Other types of retaining members may be contemplated by those skilled in the art.

As another example, FIG. 13B illustrates a portion 1220 of an object that includes a first shot of material 1222 (shown hashed). This first shot of material is molded to include a recessed portion 1224 that is of a size and shape adapted to receive article 1108 from set 1000. If desired, this recessed portion may further include posts similar to posts 1204 to mate with the holes 1110 of article 1108. A second shot of material 1226 (shown dashed) may be applied to retain article 1108 within portion 1220.

Still another example is provided by FIG. 13C, which illustrates a portion 1240 of an object that includes a first shot of molding 1242 (shown hashed). This first shot of molding includes a raised portion 1244 (shown without hash marks) that is adapted to receive cutaway portion 1114 of article 1112. If desired, a second shot of material (not shown) may be applied to embed article 1112 within portion 1240.

Figure 13D:
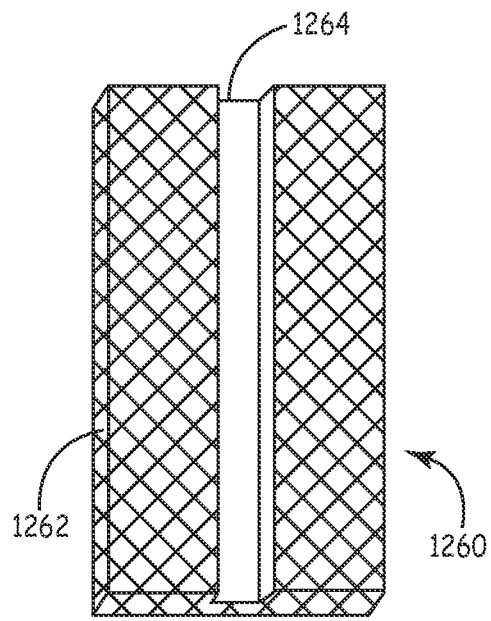

FIG. 13D illustrates another method to retain one or more radiopaque articles in position. A portion 1260 of an object formed by a first shot 1262 of material (shown hashed) includes a recessed track 1264. A portion of each of selected articles may be inserted into the track 1264 which is sized to provide a snug fit around the articles, thereby holding then) in position. If desired, a second shot of material may be applied so that the selected articles are embedded within the material.

Figure 13E:
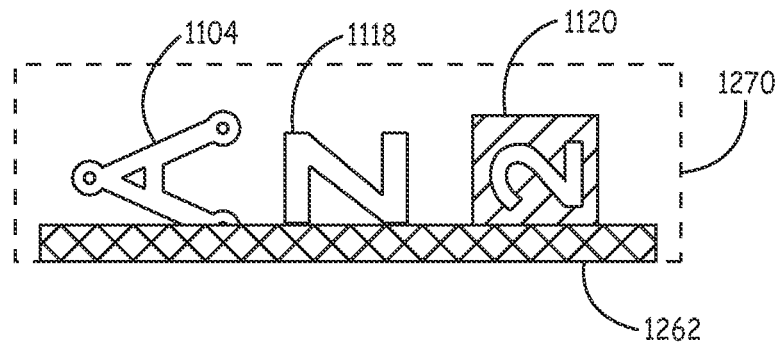

FIG. 13E is a side view illustrating how portion 1260 may be used to retain articles 1104, 1118 and 1120 from set 1100 within track 1264 during application of a second shot of material 1270 (shown dashed). Of course, if desired, the articles selected to form the marker could be oriented in a different manner before inserting them into track 1264 (e.g., so that the articles are standing "upright" relative to track 1264.)

Figure 13F:
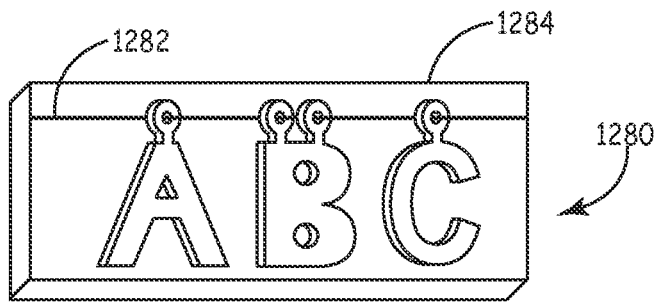

FIG. 13F illustrates yet another example of a portion 1280 of an object that may carry one or more radiopaque articles of set 1100. In this example, each article is provided with at least one eyelet (not shown in FIG. 12). In one scenario, the eyelet may lie in a plane substantially perpendicular to the plane in which the remainder of the article lies. A thread, wire or other retaining member 1282 may be inserted through the eyelets of one or more of the articles to retain them in position relative to one another. If desired, both ends of retaining member 1282 may be anchored during a molding process so that material 1284 may be applied. The resulting object will include the selected articles suspended at a desired location within the mold. This approach may provide an advantage of requiring only a single shot of material to embed the selected articles within portion 1280 of the object. Alternatively, retaining member 1282 may be otherwise anchored via adhesive, tape, by tying, or otherwise affixing it to a component of the implantable device, thereby holding the marker comprising the selected radiopaque articles in a desired location. Retaining member 1282 may, but need not, be radiopaque.

In yet another example, one or more selected radiopaque articles may be arranged within a substrate formed of a pliable biocompatible putty, paste, or clay that is not radiopaque. The resulting structure may then be encapsulated within a single shot of polymer. This method, like at of FIG. 13F, has the advantage of only requiring application of a single shot of material.

Of course, it is understood that each of FIGS. 13A-13F may illustrate only a portion of an object designed to carry one or more of articles. Thus, these mechanisms shown may be used to create a marker having any number of radiopaque articles in various spatial relationships relative to one another. For example, the object that includes portion 1200 of FIG. 13A may carry multiple radiopaque articles arranged in any manner, including an ordered sequence, a multi-dimensional array or other multi-dimensional shape or pattern. The same is true for portion 1220 of FIG. 13B and so on. Moreover, while the examples primarily include radiopaque articles from set 1100 for illustration purposes, any predetermined set of articles may be used in any of the examples.

In the illustrations described with respect to FIGS. 13A-13F, the objects carrying the radiopaque articles may be formed, at least in part, by a polymer which may be any type of polymer suitable for use within an implantable medical device, including but not limited to, the types of polymers described herein. The polymer selected for this purpose may, but need not be, optically transparent or translucent. This may allow use of visual inspections for determining the presence and/or to read the marker.

As previously discussed, an object carrying the radiopaque articles may be a component of the implantable medical device such as a header block, an insulator cup assembly, or some other type of assembly that provides some function besides the marker function within the implantable device. Alternatively, the object that directly carries the radiopaque articles may be a marker object which has no other purpose other than to retain the radiopaque articles relative to one another, with that marker object then being carried by yet another object within the IMD.

Figure 14A:
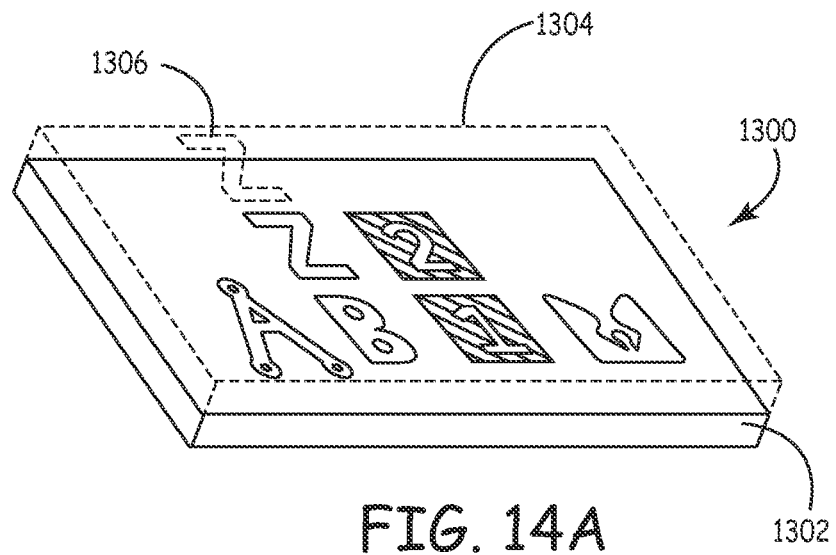
FIG. 14A is a perspective view of a marker object including one or more articles from a predetermined set.

FIG. 14A illustrates marker object 1300 including one or more articles from set 1100. These articles may be arranged in a selected manner upon a first shot 1302 of material and retained in positioned in any of the ways described above or any other way suitable for retaining these articles with features such as complementary posts and apertures.). For instance, the articles may be arranged in a multi-dimensional (e.g., two- or even three-dimensional) array. As an example, article 1306 (shown dashed) may be positioned within a different plane than the remainder of articles included within marker object 1300. Alternatively, the articles may be arranged in some other two or three dimensional pattern a star shape, etc.), with three dimensional patterns being created using a multi-shot molding process and/or three dimensional molds. A second shot 1304 of material (shown dashed) may be applied, if desired.

Figure 14B:
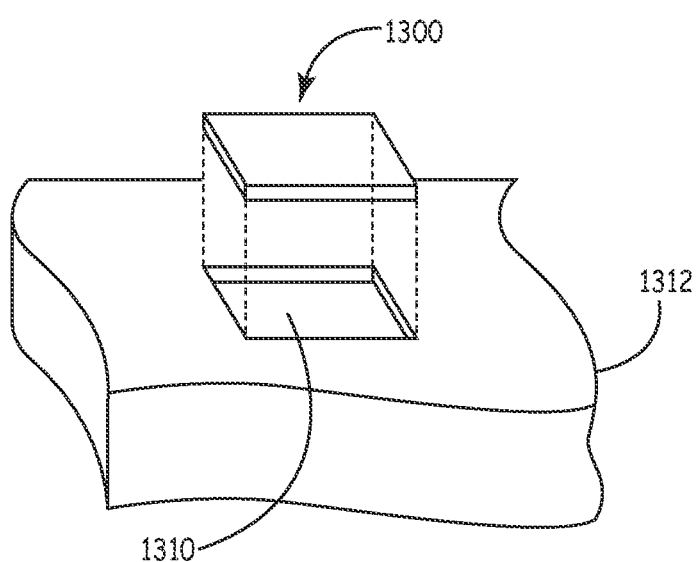
FIG. 14B is a perspective view of a marker object being received by a recessed space of a larger object.

The resulting marker object of this example may not serve any purpose other than to carry the selected one or more radiopaque articles from the predetermined set. This marker object 1300 may then be affixed to, embedded within, or otherwise carried, by another component of the IMD. For instance, FIG. 14B shows marker object 1300 being fitted into position in a recessed space 1310 of a larger object 1312, which may be a cup assembly, a portion of a header block, or some other component that serves a purpose within the implantable medical device beyond the marker function. If desired, yet another shot of material may be applied to embed marker object 1300 into larger object 1312. For instance, an over-mold layer may be applied to all, or a portion, of object 1312 after marker object 1300 is positioned within recessed space 1310.

In any of the foregoing examples of FIGS. 13A-13F and 14A-14B, one or more radiopaque articles may be embedded within an object using multiple shots of material. However, this is not necessary. For instance, returning to FIG. 14A, the mating of posts 1204 with the apertures of tabs 1102 may be sufficient to retain article 1104 in position such that a second shot 1206 of material is deemed unnecessary. In this case, the articles may be retained solely by the first shot of material.

It will be understood that the techniques described in relation to these figures do not necessarily require use of a polymer and many of these techniques can be used to retain the radiopaque articles on components of the IMD that are made of a material other than a polymer. For instance, an inner wall of the can of the implantable medical device, which may be formed from titanium or some other biocompatible metal, may be fitted with features similar to posts 1204, recess 1224, or raised portion 1244. Such retaining features may be designed to mate with complementary features of a respective radiopaque article. These mating elements may be used alone, or with some other fixation mechanism to ensure the position of the radiopaque articles is maintained. For instance, in one case, an adhesive may be used to further affix the radiopaque articles to the object. Additionally or alternatively, a layer of epoxy or other lamination may be applied over a portion of the surface of the radiopaque articles and the object carrying those articles to affix the articles to the object. A one- or two-sided tape may alternatively or additionally be applied to maintain the radiopaque articles in position.

Figure 15A:
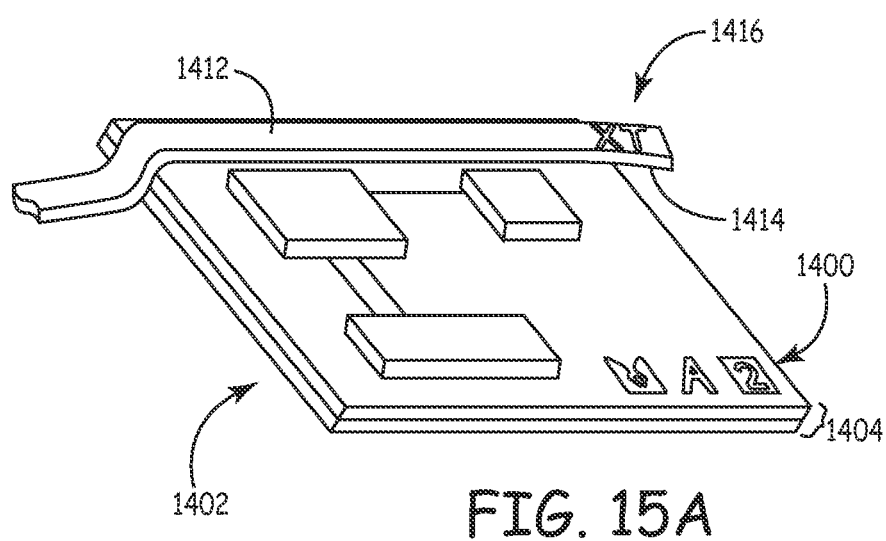
FIG. 15A is a perspective view of yet another example of a marker formed from one or more selected ones of a predetermined set of radiopaque articles.

FIG. 15A illustrates yet another example of a marker 1400 formed from selected radiopaque articles that are arranged relative to one another to form a marker. In this example, three radiopaque articles are carried on a circuit board 1402 which may utilize flexible circuit technology. As is known in the art, such technology may comprise various electronic devices that are mounted on a flexible substrate which may be made from aplastic, polyester, polyethylene terephthalate (PET), a polyimide, PEEK, or other suitable flexible materials. In one case, the radiopaque articles may be positioned and retained between multiple layers 1404 of the circuit board. For example, the radiopaque articles may be heat-sealed into the flexible layers. Since the radiopaque articles are generally formed from a material that is electrically conductive, it is important to ensure that the radiopaque articles do not cause any inadvertent electrical connections between electrical traces and other electrical circuitry associated with the circuit board.

In another instance, the articles included in marker 1400 may be retained on a surface of the circuit assembly using a tape such as pressure-sensitive adhesive (PSA) tape. Alternatively or additionally, a laminating layer may be applied over the articles to hold them in place and electrically insulate them from other circuit components.

FIG. 15A further illustrates another example of using a tape such as a pressure-sensitive acrylic adhesive (PSA) tape to carry a marker comprising multiple radiopaque articles. In this example, a piece of tape 1412 is affixed to a surface of the circuit board, as may be useful in stabilizing the circuit board 1402 to another surface and/or to secure a component to the circuit board 1402. An extra tab 1414 has been created by the tape, which may be double-sided tape having adhesive on both sides. This tab may be used to carry a second marker 1416.

Figure 15B:
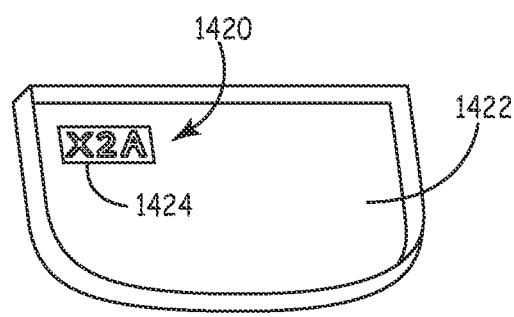
FIG. 15B is a perspective view illustrating securing a marker to an object of IMD.

FIG. 15B is yet another example of securing a marker to an object that has some functionality beyond providing the marker function. In one example, the one or more radiopaque articles 1420 may be secured directly to the inside of a portion of the can 1422 of the implantable device. The radiopaque articles may be secured using any one or more of the techniques described above, including use of a piece of tape 1424. As previously discussed, this could alternatively be accomplished using an adhesive material, a layer of epoxy applied over the radiopaque articles, and/or one or more features of the can that mate with complementary features of the radiopaque articles, in an alternative example, individual radiopaque articles may be affixed one to another first using a marker object comprised of polymer or another material. That marker object can then be affixed to can 1422 in any suitable manner, including using any of the techniques described herein.

Thus, according to one aspect of the disclosure, techniques are provided for qualifying a set of radiopaque articles. One or more articles may then be selected from the set for use in creating multiple markers for various makes and models of IMDs without being required to undergo further qualification procedures, saving both time and other resources.

As previously described, the radiopaque articles can be made of any suitable radiopaque material. The radiopaque material selected for this purpose may be biocompatible, although biocompatibility may not be necessary if the radiopaque is enclosed in a hermetic device. Such materials include tungsten, tantalum, platinum, gold, barium silicate, as well as alloys such as Hastelloy® metals. Various processes exist for forming the radiopaque articles from such materials. In one instance, an etching process is used to create the articles in the set. This process may be a photo etching process whereby a photo-resistive coating is applied as a mask to a light-sensitive polymer plate. Light is projected onto the plate and the plates are then washed to remove the photo-resistive material that was used as the mask. An additional washing step may then be used to chemically remove the portion of the metal that was exposed to the light. In another embodiment, the photo-resistive coating and the exposed metal may be removed in one washing step. Other similar etching processes may be used as are known to those skilled in the art.

Another mechanism for creating the radiopaque articles involves punching the articles from a sheet of radiopaque material. For instance, a ribbon of material may be fed into a die set having male and female portions that stamp out the characters in one case, the punched articles may not be entirely separated one from another during the punching process but may remain connected to a larger sheet of such articles via break-away tabs. Prior to use, a desired article may be separated from the larger sheet of articles by twisting, bending, cutting, or otherwise breaking the respective tab. This allows the articles, which may individually be very small, to be readily stored and managed as a group until just prior to use. Such a punching process, as well as the use of break-away tabs, may produce radiopaque articles having jagged edges and/or burrs.

Yet another technique for producing the radiopaque articles involves using a laser cutting technique. Laser cutting can produce very tight tolerances and smooth edges, aiding readability of small radiopaque markers. However, some materials may be expensive or difficult to process using this method. In particular, this method may be expensive at higher volume production levels.

Still another option for creating the radiopaque articles involves a sintering process. According to this method, powdered radiopaque material mixed with glue is pressed into a form and baked until all of the glue has been dissipated and the radiopaque particles bind together. This type of process creates a porous structure which may more readily adhere to the molecules of a polymer used during a subsequent molding process, with the degree to which the polymer is received by the pores being dependent upon molecular size of the polymer.

Metal injection molding may also be used to create the radiopaque articles. In this scenario, a radiopaque powder or slurry is injected under pressure into a mold. The powder or slurry is then baked until the radiopaque particles bind one to another. As with sintering, this may produce a relatively more porous radiopaque article.

Figure 16:
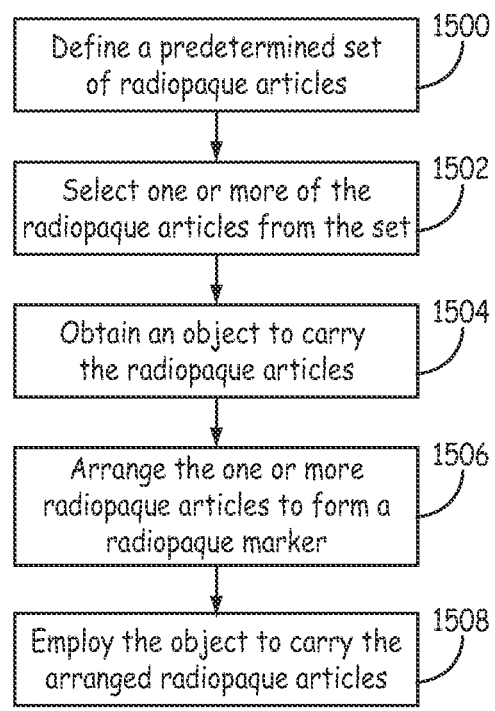
FIG. 16 is a flow diagram of one method according to the current disclosure.

FIG. 16 is one method according to the current disclosure. A predetermined set of radiopaque articles may be defined (1500). As discussed, this predetermined set may include predefined characters (e.g., alphanumeric characters, predefined symbols, and so on) and/or arbitrary symbols. Such a set may include articles that will project a positive image and/or articles that will project a negative image when viewed with imaging technology.

One or more of the radiopaque articles may be selected from the set (1502). The articles may be selected to convey information about an IMD that will carry those articles, including make, model, a feature set, and so on.

An object may then be obtained to carry the radiopaque articles (1504). Such an object may be a marker object having the purpose of retaining the selected articles in a predetermined relationship relative to one another. The object may alternatively be some component of the IMD having some purpose beyond the marker function.

The radiopaque articles may be arranged on the obtained object to form a radiopaque marker (1506). The arrangement, as well as the articles contained in the arrangement, may be used to convey information about the IMD. The object is then employed to carry the arranged radiopaque articles (1508). This may be accomplished by affixing or otherwise causing the articles to be carried by the object in the selected arrangement according to any of the mechanisms described herein or variations thereof as may be contemplated by those skilled in the art.

Figure 17:
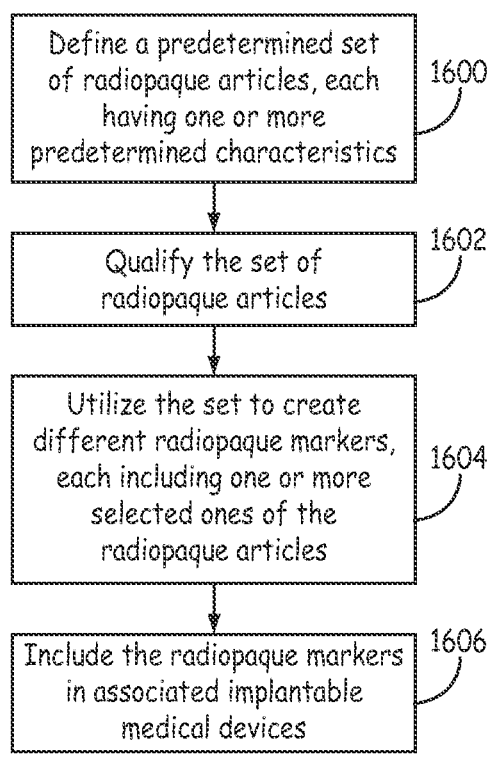
FIG. 17 is a flow diagram of another method according to the current disclosure.

FIG. 17 is another method according to the current disclosure. A predetermined set of radiopaque articles may be defined, with each article in the set optionally having one or more predetermined characteristics (1600). For instance, all articles in the set may have one or more physical dimension that is within a predetermined range. The articles in the set may each be formed of a same material, have a common feature used to affix them to another object, and/or have one or more other common characteristics. The set of radiopaque articles may be qualified for quality assurance to allow any selected combination of the radiopaque articles to be included in a marker of an IMD (1602). As discussed above, such a qualification process may define quality control aspects of the articles such as ensuring that each such article is safe and can be reliably re-produced and inspected. The set of articles may then be used to create different radiopaque markers, each including one or more of the radiopaque articles (1604). Each of the radiopaque markers may be included in a respectively-associated implantable medical device for use in conveying information about the TMD (1606).

Thus, embodiments of RADIOPAQUE EMBEDDED INTO DESICCANT FOR IMPLANTABLE MEDICAL DEVICE are disclosed. One skilled in the art will appreciate that the apparatuses and methods described herein can be practiced with embodiments other than those disclosed. The disclosed embodiments are presented for purposes of illustration and not limitation.

What is claimed is:

1. An implantable medical device (IMD), comprising:
 a radiopaque marker comprising multiple radiopaque articles arranged in a predetermined manner;
 a housing; and
 a desiccant article carrying the radiopaque marker, wherein the desiccant article and the radiopaque marker carried by the desiccant article are disposed in the housing.

2. The IMD of claim 1, wherein the radiopaque articles are selected from a predetermined set of radiopaque articles, each of the radiopaque articles in the set having at least one characteristic in common with other radiopaque articles in the set.

3. The IMD of claim 2, wherein the at least one characteristic is a physical dimension.

4. The IMD of claim 1, wherein the radiopaque articles comprise alphanumeric characters formed of radiopaque material.

5. The IMD of claim 1, wherein the radiopaque articles indicate one or more of a manufacturer, a type of the IMD, a model of the IMD, features of the IMD, a date associated with the IMD, and a location associated with the IMD.

6. The IMD of claim 1, wherein the radiopaque articles are formed of tungsten.

7. The IMD of claim 1, wherein the desiccant article carrying the radiopaque marker comprises one or more features adapted to retain the radiopaque articles in a predetermined arrangement.

8. The IMD of claim 7, wherein the one or more features are adapted to mate with one or more features of the radiopaque articles.

9. The IMD of claim 1, wherein the multiple radiopaque articles comprise features adapted to retain the radiopaque articles with respect to the desiccant article carrying the radiopaque marker.

10. The IMD of claim 1, wherein the radiopaque articles comprise at least one arbitrary symbol formed of radiopaque material.

11. The IMD of claim 1, wherein the one or more radiopaque articles are at least partially embedded in the desiccant article.

12. The IMD of claim 1, wherein the one or more radiopaque articles are completely embedded within the desiccant article.

13. The IMD of claim 1, wherein the one or more radiopaque articles are affixed to the desiccant article with an adhesive or a tape.

14. The IMD of claim 1, wherein the one or more radiopaque articles are impregnated in the desiccant article.

15. The IMD of claim 1, wherein the predetermined set of multiple radiopaque articles undergo a qualification process to allow any combination of the multiple radiopaque articles to be selected for inclusion in the IMD.

16. The IMD of claim 1, further wherein the housing is hermetically sealed.

17. The IMD of claim 1, wherein the desiccant article comprises an over-molded polymer.

18. The IMD of claim 17, wherein the over-molded polymer is optically transparent.

* * * * *